United States Patent [19]

Aall-Flood et al.

[11] Patent Number: 4,846,787
[45] Date of Patent: * Jul. 11, 1989

[54] APPARATUS FOR PREVENTING BACK-FLOW OF FLUID IN A BLOOD FILTERING SYSTEM

[75] Inventors: Kjell J. Aall-Flood, Trelleborg; Per-Olof A. V. Carlsson, Sosdala, both of Sweden

[73] Assignee: Gambro AB, Sweden

[*] Notice: The portion of the term of this patent subsequent to Mar. 17, 2004 has been disclaimed.

[21] Appl. No.: 910,071

[22] Filed: Sep. 22, 1986

[30] Foreign Application Priority Data

Oct. 28, 1985 [SE] Sweden ............................ 8505075

[51] Int. Cl.⁴ .............................................. A61M 37/00
[52] U.S. Cl. ................................. 604/5; 604/30; 604/45; 604/246; 210/136; 210/321.3
[58] Field of Search ............... 604/4, 5, 6, 321, 247, 604/30, 246, 45, 126; 128/DIG. 3; 210/927, 136, 321.2, 321.3

[56] References Cited

U.S. PATENT DOCUMENTS

| | | | |
|---|---|---|---|
| 3,046,903 | 7/1962 | Jones | 604/153 |
| 3,064,649 | 11/1962 | Fuson | 128/DIG. 3 |
| 3,191,600 | 6/1965 | Everett | 604/247 |
| 3,417,750 | 12/1968 | Carson | 604/247 |
| 3,463,159 | 8/1969 | Heimlich | 604/321 |
| 3,525,357 | 8/1970 | Koreski | 604/247 |
| 3,649,138 | 3/1912 | Clay et al. | 417/477 |
| 4,012,217 | 3/1977 | Yakich | 417/477 |
| 4,650,458 | 3/1987 | Dahlberg et al. | 604/5 |

Primary Examiner—Stephen C. Pellegrino
Assistant Examiner—Colleen M. Reilly
Attorney, Agent, or Firm—Lerner, David, Littenberg, Krumholz & Mentlik

[57] ABSTRACT

A blood filtering system includes a check valve for preventing fluid back-flow, coupled between a peristaltic pump and a pressure equalizer, the valve including a tubular container having an inlet and an outlet, two elongated plastic films in the container extending from the inlet facing each other, joined at their peripheries, with a hole in an end of one film proximate the container outlet. Fluid may flow from the inlet through the films to the outlet; but, back-flow is prevented by collapse of the films.

22 Claims, 2 Drawing Sheets

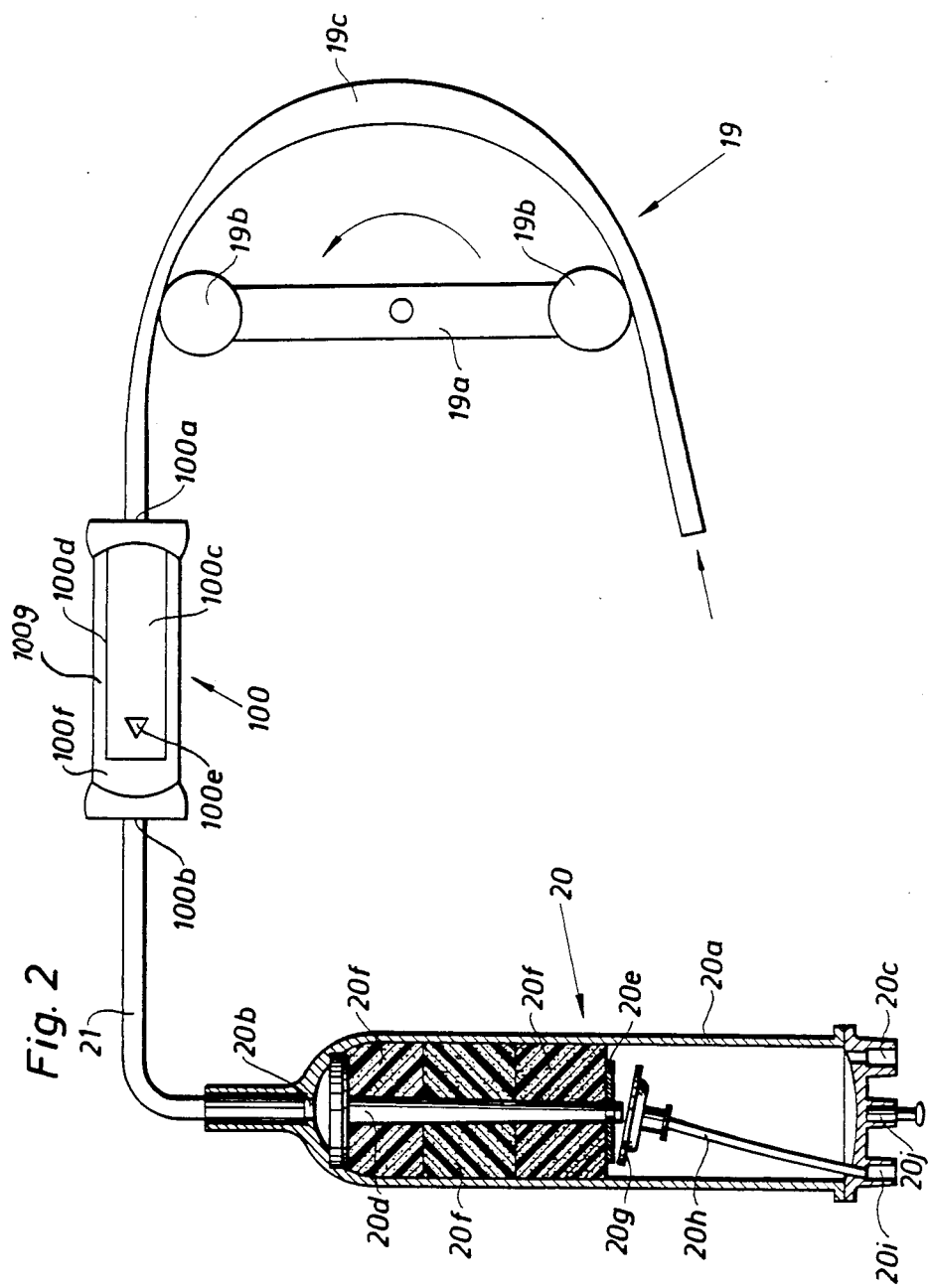

APPARATUS FOR PREVENTING BACK-FLOW OF FLUID IN A BLOOD FILTERING SYSTEM

FIELD OF THE INVENTION

The present invention relates generally to apparatus for preventing the back-flow of fluid, and more particularly to such apparatus employed in a blood filtering system.

An apparatus in accordance with the present invention has many applications. It is intended in particular, though, to form part of a blood filtering system of the type having means for withdrawing blood from the patient or some other source; a filter, with the help of which a filtrate can be withdrawn from the blood; a peristaltic pump for moving the filtrate; means for returning the remainder of the blood to the source together with any replacement fluid; and, a measuring device for measuring the amount of filtrate withdrawn.

The system may be used for hemofiltration or plasmapheresis, in which a replacement fluid is supplied in place of the withdrawn filtrate. It will be clear, however, to those of ordinary skill in the art that the invention can also be applied to other systems, such as in conjunction with hemodialysis, when the dialysis is combined with the removal of an ultrafiltrate.

BACKGROUND OF THE INVENTION

The overall process of hemofiltration which is carried out at the same time as preparation of a replacement fluid is shown, for example, in European Patent Application Nos. EP 0 042 939 and EP 0 087 171, respectively.

Plasmapheresis differs from hemofiltration primarily in that it requires a slightly more permeable membrane material so that even larger molecules can be filtered out therewith.

Examples of suitable hemofiltration membranes are described in European Patent Application No. EP 0 046 816. Similarly, suitable membranes for plasmapheresis are described in European Patent Application No. EP 0 044 958. It will be clear, however, to those of ordinary skill in this art, that other membranes can also be used in conjunction with the realization of the present invention.

When in the past it has been necessary to measure the amounts of filtrate withdrawn in conjunction with processes such as hemofiltration or plasmapheresis, it has been found to be quite difficult to carry out exact measurements due to variations in the pressure conditions and consequent varying flow conditions therein. In particular, specific problems were encountered with peristaltic pumps normally used in such processes. These types of pumps act on the outside of flexible blood tubes in a pulsating manner.

The above-mentioned problem has been largely solved with the help of a system which is described in more detail in European Patent Application No. 85.106708.2. This was achieved with the help of a device for equalizing the pressure in the filtrate flow which passes through the measuring device. In this way, the certainty of the measurement was improved substantially, though not completely satisfactorily. It is suspected that the residual uncertainty is due to the microbubbles formed during the pumping which pass through the pressure equalizing device that is designed to separate air from the filtrate.

SUMMARY OF THE INVENTION

In accordance with the present invention, an apparatus is provided for preventing back-flow of fluid, which comprises a first container having an inlet and an outlet; and, a collapsible second container, disposed in the first container, having an open end coupled to the inlet, and having a hole therein.

In a preferred embodiment of the apparatus of the present invention, the collapsible second container comprises a first film extending from the inlet, and a second film extending from the inlet, with the first film facing the second film, and the first and second films being joined along their peripheries. The films are elongated along an axis extending from the opening of the second container to the end of the second container opposite the opening. The first container is tubular, and the hole is triangular and disposed on the end of one of the films, proximate the outlet of the first container.

In accordance with the present invention, a blood filtering system is provided which comprises a peristaltic pump, and a check valve, coupled to the pump downstream thereof, for preventing fluid back-flow through the pump.

In accordance with the present invention, an apparatus is provided for the measurement of a filtrate separated from a supply of blood and replacement of the filtrate with a replacement fluid as a substitute for the filtrate in the blood, comprising: measuring means for measuring the amount of the filtrate flowing therethrough; first conduit means for continuously delivering the filtrate to the measuring means; second conduit means for supplying an amount of a replacement fluid as a substitute for the measured amount of the filtrate; pump means associated with the first conduit means for drawing the filtrate through the first conduit means into the measuring means; pressure equalizing means associated with the first conduit means and located at a point in the first conduit means between the pump means and the measuring means for equalizing the pressure in the filtrate flowing through the first conduit means; and, the above-described apparatus for preventing backflow of fluid, coupled between the pump means and the pressure equalizing means.

In a preferred embodiment of this apparatus of the present invention, the pump means comprises a peristaltic pump, the apparatus for preventing back-flow of fluid comprises the preferred embodiment thereof described above, and the pressure equalizing means comprises a drip chamber adapted to serve as an air separating device.

The apparatus of the present invention for preventing back-flow of fluid, when utilized in the above-described blood filtering system, coupled between the pump means and the pressure equalizing means, provides certain advantages. When used in connection with the pumping of blood, for example, it can eliminate the damage to blood resulting from back-flow through a pump, such as a peristaltic pump. Further, it eliminates dangerous microbubbles formed by back-flow, which can pass through the pressure equalizing device. This has been confirmed with areometer measurements. Back-flow is effectively prevented by the present invention which, owing to its design, can be so inexpensively manufactured that it may be discarded after a single use.

BRIEF DESCRIPTION OF THE DRAWINGS

FIG. 2 is a side, elevational, partially sectional view of a pressure equalizing device, a side elevational view of a check valve, and a schematic diagram of a peristaltic pump, depicting components of the system of FIG. 1.

DETAILED DESCRIPTION

Figure 1:
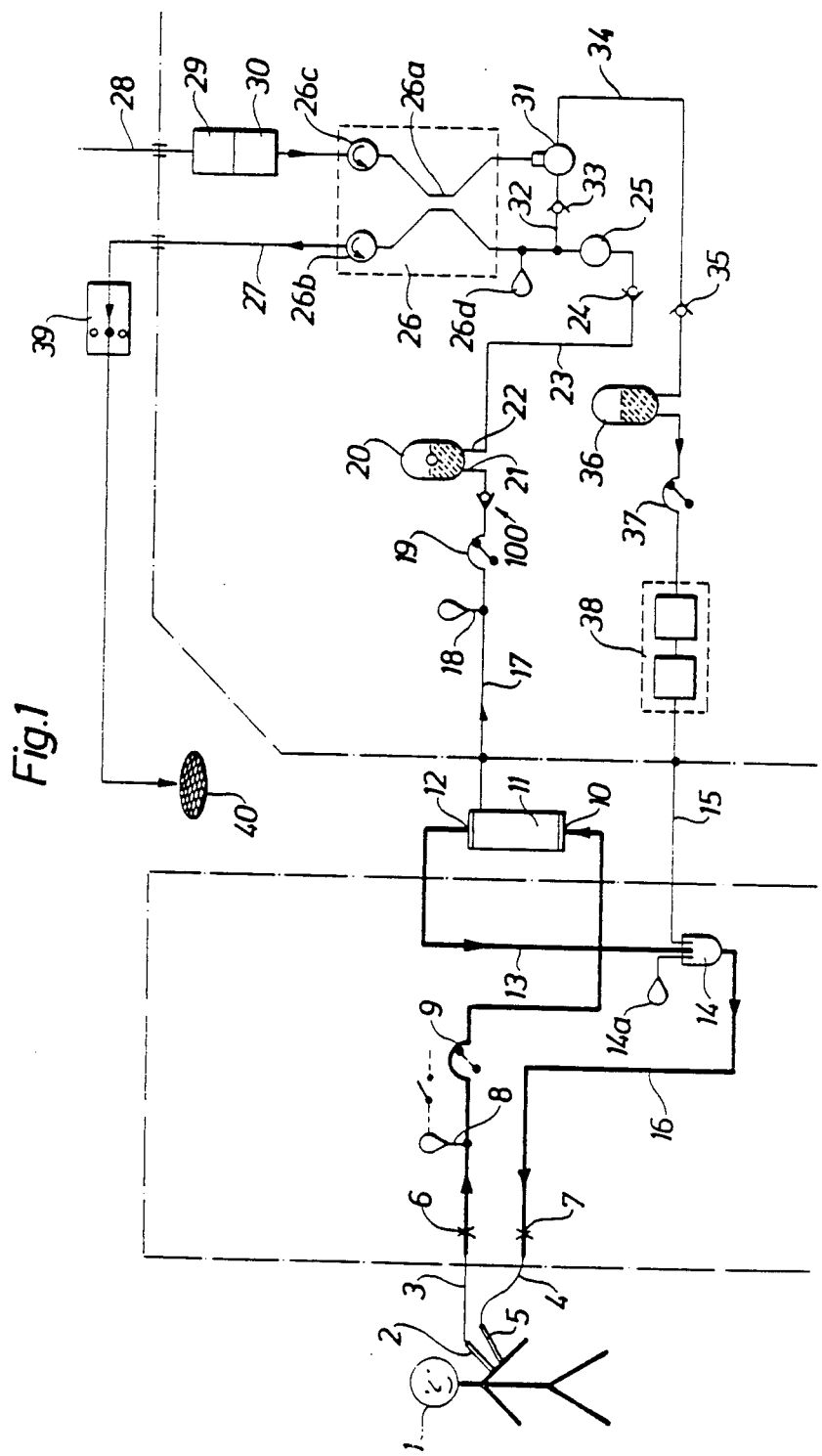
FIG. 1 is a schematic diagram of a preferred overall system used in connection with the present invention.

Turning now to the drawings, in which like numerals refer to like portions thereof, in the block diagram shown in FIG. 1, a patient is designated 1. Blood is withdrawn from patient 1 by means of a cannula 2, and is then conducted through duct 3 into a blood treatment system. The blood is eventually returned to the patient through duct 4 and cannula 5. For reasons of safety, these ducts 3 and 4 can be shut off and opened with the help of clamps 6 and 7, respectively. After clamp 6, the blood passes an arterial pressure gauge 8, which is arranged upstream of a peristaltic pump 9, by means of which circulation of the blood in the system is achieved. From the pump 9 the blood is pressed through inlet 10 into filter 11, and then out of filter 11 through outlet 12.

The invention is particularly intended to be utilized in conjunction with hemofiltration or plasmapheresis, and the filter thus shown in FIG. 1 is a hemofilter or a plasmapheresis filter, respectively. The scope of the present invention, however, is not intended to be limited to these particular examples.

From outlet 12, the blood passes through duct 13 to drip chamber 14, which is coordinated with a venous pressure gauge 14a. A replacement fluid is also conducted to the drip chamber 14, through a duct 15. From the drip chamber, the blood mixed with replacement fluid is then conducted via duct 16, clamp 7 and cannula 5, back to the patient 1.

From the filter 11, filtrate is withdrawn through a duct 17, the pressure being measured by means of a pressure gauge 18. In order to draw the filtrate out of the filter 11, a pump 19 is utilized. This pump 19 is preferably a conventional peristaltic pump.

A check valve 100 is inserted in accordance with the present invention which will be described in greater detail in connection with FIG. 2 and which effectively prevents any back-flow into the peristaltic pump 19. After the check valve 100, the filtrate then passes into a pressure equalizing device 20, which too will be described in greater detail in connection with FIG. 2. The inlet to the pressure equalizing device is designated 21, and the outlet is designated 22. The filtrate is then passed by means of a duct 23, via a check valve 24, and a suitable, controllable ultrafiltration valve 25 to a flow meter 26. This may be designed, for example, in accordance with the European Patent Application No. EP 0 106940, but other designs can, of course, be substituted therefor.

From the meter 26 the filtrate passes through duct 27 either to a collecting point, if it is to be retained, or to a drain 40.

A replacement fluid prepared in a separate set-up is supplied to the meter 26 through duct 28, conductivity meter 29, and temperature measuring device 30.

The meter 26 preferably comprises a first part 26a, which is used to measure the difference between flows in the ducts 27 and 28. Moreover, as a check, measurement of the individual flows in parts 26b and 26c can also take place. Furthermore, in order to effect possible adjustments in the measured flow on the basis of the temperature, meter 26 may be coordinated with a temperature measuring device 26d. From meter 26, the replacement fluid is delivered to a valve 31, which on the basis of the values measured on measuring devices 29 and 30 then conducts replacement fluid either to a by-pass duct 32, via check valve 33, and from there to discharge pipe 27, or to a duct 34, and via check valve 35, to pressure equalizing device 36, infusion pump 37, and possibly to a filter system 38, a duct 15, and then to drip chamber 14.

Finally, number 39 in FIG. 1 designates a valve which allows flow only when pressure exists in the system, but which immediately terminates the connection to drain 40 if the pressure measured at that point is greater than that in the remainder of the system. In such a case, an air gap is then created, so that it becomes impossible for fluid to be conducted from the drain 40 back into the system.

In FIG. 2 are shown some preferred designs of components and, more particularly, the pump 19, the check valve 100 and the pressure equalizing device 20. The pump 19 is shown schematically as a conventional peristaltic pump comprising a rotor 19a with two rollers 19b which are adapted to press a pump segment 19c against a holding-up element not shown. With the help of the pump the filtrate is forced into the check valve 100. The filtrate enters an inlet 100a of a first container 100g. An open end of a collapsible second container 100c is coupled to the inlet 100a. The filtrate flows into the second container 100c, and out through a hole 100e therein, preferably polygonal, particularly, triangular in shape. The filtrate then passes into a padlike outer part 100f of the first container 100g, and then leaves the check valve 100 via an outlet 100b of the first container 100g. In response to filtrate entering the outlet 100b, the second container 100c collapses, thereby preventing back-flow. Preferably, the collapsible second container 100c comprises two thin, elongated plastic films extending from the inlet 100a. The plastic films face each other, and are joined along their peripheries 100d. The first container 100g is preferably tubular in shape.

From the check valve the filtrate flows via the duct 21 to the pressure equalizing device 20 which has been given a modified design as compared with that shown in FIG. 1. More particularly, the pressure equalizing device 20 comprises an outer shell 20a with an inlet 20b and an outlet 20c. Three annular defrothing elements 20f are suspended with the help of a rod 20d and a lock washer 20e. They may consist, for example, of a polyurethane foam coated with a special defrothing agent. As described in greater detail in the above-mentioned European Patent Application No. 85. 106708.2, the level in the device 20 is maintained constant with the help of a gas-permeable but liquid-tight membrane 20g which communicates via a duct 20h with an air outlet 20i. Numeral 20j designates an extra outlet which may be used, for example, for sampling or the like. U.S. Pat. No. 4,198,971 describes a drip chamber of similar design.

It will be understood that the embodiments described herein are merely exemplary and that a person skilled in the art may make many variations and modifications without departing from the spirit and scope of the invention. All such modifications and variations are intended to be included within the scope of the invention as defined in the appended claims.

What is claimed is:

1. An apparatus for the measurement of a filtrate separated from a supply of blood and replacement of said filtrate with a replacement fluid as a substitute for said filtrate in said blood, comprising:

measuring means for measuring the amount of a fluid flowing therethrough;

first conduit means for continuously delivering said filtrate to said measuring means whereby said filtrate can flow through said measuring means and said amount of said filtrate can be measured thereby;

second conduit means for supplying an amount of a replacement fluid corresponding to said measured amount of said filtrate as a substitute therefor whereby said amount of said replacement fluid can replace said filtrate separated from said supply of blood;

pump means associated with said first conduit means for drawing said filtrate through said first conduit means into said measuring means, said pump means comprising a peristaltic pump; and a check valve coupled to said peristaltic pump, located immediately downstream thereof, and in fluid communication therewith, for preventing fluid back-flow through said peristaltic pump.

2. An apparatus as in claim 1, including pressure equalizing means associated with said first conduit means and located at a point in said first conduit means downstream from said check valve and upstream of said measuring means for equalizing the pressure in said filtrate flowing through said first conduit means, whereby said check valve is located between said peristaltic pump and said pressure equalizing means.

3. An apparatus as in claim 1 or 2 wherein said check valve comprises a first container having an inlet and an outlet, and a collapsible second container disposed in said first container, said collapsible second container having an open end coupled to said inlet, and having a hole therein.

4. An apparatus as in claim 3 when said collapsible second container comprises a film.

5. An apparatus as in claim 4 wherein said film comprises a first film extending from said inlet, and a second film extending from said inlet, said first film facing said second film, said first and second films being joined along peripheries thereof.

6. An apparatus as in claim 5 wherein said hole is disposed on an end of said collapsible second container opposite said opening, and said first and second films are elongated along an axis extending from said opening to said end.

7. An apparatus as in claim 6 wherein said first container comprises a tubular container, said hole is disposed proximate to said outlet, and said hole comprises a polygonal hole.

8. An apparatus as in claim 7 wherein said polygonal hole comprises a triangular hole.

9. An apparatus as in claim 2 wherein said pressure equalizing means comprises a drip chamber adapted for separating air from said filtrate.

10. A blood filtering system comprising: a peristaltic pump; and a check valve, coupled to said peristallic pump immediately downstream thereof and in direct fluid communication therewith for preventing fluid back-flow through said pump, wherein said check valve comprises:

a first container, having an inlet and an outlet; and a collapsible second container, disposed in said first container having an open end coupled to said inlet, and having a hole therein, whereby fluid can flow downstream through said collapsible second container without resistance therefrom.

11. An apparatus as in claim 10 wherein said collapsible second container comprises a film.

12. An apparatus as in claim 11 wherein said film comprises a first film extending from said inlet, and a second film extending from said inlet, said first film facing said second film, said first and second films being joined along peripheries thereof.

13. An apparatus as in claim 12 wherein said hole is disposed on an end of said collapsible second container opposite said opening, and said first and second films are elongated along an axis extending from said opening to said end.

14. An apparatus as in claim 13 wherein said first container comprises a tubular container, said hole is disposed proximate said outlet, and said hole comprises a polygonal hole.

15. An apparatus as in claim 14 wherein said polygonal hole comprises a triangular hole.

16. A blood filtering system comprising:

a peristaltic pump;

a check valve, coupled to said peristaltic pump immediately downstream thereof and in direct fluid communication therewith, for preventing fluid back-flow through said pump, said check valve comprising a first container having an inlet and an outlet, and a collapsible second container disposed from said first container said collapsible second container having an open end coupled to said inlet, and having a hole therethrough; and pressure equalizing means coupled to said check valve and downstream thereof for equalizing the pressure in said fluid flowing through said pump, said check valve thereby being located between said peristaltic pump and said pressure equalizing means.

17. An apparatus as in claim 16 wherein said collapsible container comprises a film.

18. An apparatus as in claim 17 wherein said film comprises a first film extending from said inlet, and a second film extending from said inlet, said first film facing said second film, said first and second film being joined along peripheries thereof.

19. An apparatus as in claim 18 wherein said hole is disposed on an end of said collapsible second container opposite said opening, and said first and second films are elongated along an axis extending from said opening to said end.

20. An apparatus as in claim 19 wherein said first container comprises a tubular container, said hole is disposed proximate to said outlet, and said hole comprises a polygonal hole.

21. The apparatus of claim 20 wherein said polygonal hole comprises a triangular hole.

22. An apparatus as in claim 16 wherein said pressure equalizing means comprises a drip chamber adapted for separating air from said fluid.

* * * * *